United States Patent [19]

Stahmann et al.

[11] 3,979,508
[45] Sept. 7, 1976

[54] COMPOSITIONS AND METHODS THEREWITH FOR PENICILLIN HYPERSENSITIVITY DETECTION

[75] Inventors: Mark A. Stahmann, Madison; Sudhakar S. Wagle, Mequon, both of Wis.

[73] Assignee: Kremers-Urban Company, Milwaukee, Wis.

[22] Filed: Jan. 10, 1975

[21] Appl. No.: 539,987

Related U.S. Application Data

[60] Division of Ser. No. 274,325, July 24, 1972, Pat. No. 3,867,365, which is a continuation-in-part of Ser. No. 61,514, Aug. 5, 1970, abandoned, which is a continuation-in-part of Ser. No. 656,323, July 27, 1967, abandoned.

[52] U.S. Cl. .................................. 424/9; 424/12; 424/78; 424/85; 424/88; 424/177
[51] Int. Cl.² ............... A61K 29/00; A61K 31/43; A61K 37/02
[58] Field of Search ............... 424/9, 12, 78, 85, 88, 424/177; 260/112.5

[56] References Cited
OTHER PUBLICATIONS

Parker, J. Lab. & Clin. Med, vol. 62, 1963 p. 482.
Levine, J. of Med. Chem., vol. 7, 1964, p. 675.
Fellner, J. of Allergy, vol. 36, 1965, p. 342.

*Primary Examiner*—James O. Thomas, Jr.
*Assistant Examiner*—A. P. Fagelson
*Attorney, Agent, or Firm*—Henry L. Brinks

[57] ABSTRACT

The stereo-isomeric penicilloyl-polylysine conjugates having high optical dextro-rotations are useful for eliciting cutaneous responses in persons with penicillin hypersensitivity.

The process for manufacturing the above-entitled stereo-specific conjugates reacts penicillin with neutralized polylysine hydrochloride in a non-aqueous polar solvent such as dimethyl sulfoxide.

22 Claims, No Drawings

COMPOSITIONS AND METHODS THEREWITH FOR PENICILLIN HYPERSENSITIVITY DETECTION

CROSS REFERENCE TO RELATE APPLICATIONS

This application is a division of application Ser. No. 274,325, filed July 24, 1972, now U.S. Pat. No. 3,867,365, the latter of which is a continuation-in-part of application Ser. No. 61,514, filed Aug. 5, 1970, now abandoned which in turn is a continuation-in-part of application Ser. No. 656,323 filed July 27, 1967, now abandoned.

BACKGROUND OF THE INVENTION

1. Field of the Invention

This invention relates to penicilloyl-polylysine conjugates useful for eliciting cutaneous responses in persons having penicillin hypersensitivity and to processes for the manufacture of such compositions.

2. Discussion of the Prior Art

It is well known that significant proportions of the population are hypersensitive to penicillin. Individual allergic reactions to penicillin range from urticaria to acute anaphylactic shock, the latter which is frequently fatal. It is highly desirable, therefore, to provide means for readily identifying patients who may have penicillin allergy, and more particularly, a means to identify those patients who may become victims of anaphylactic shock.

Existing procedures for screening patients for allergic reactions to penicillin, however, are not entirely reliable. In addition, the skin tests heretofore employed have not been completely reliable.

Penicillin itself is unsatisfactory for skin testing for many reasons. For example, testing results are often times erratic. In addition, penicillin may sensitize the patient, it may produce shock, or it may not produce reactions to the degradation products of penicillin to which the patient may be hypersensitive.

It has been necessary, therefore, to discover other procedures, methods, compounds, and compositions that may indicate penicillin hypersensitivity. Consequently, many different materials have been investigated and significant amounts of research have been devoted to this problem. The many years of study and effort, however, have resulted in a wide variety of proposals.

One publication of reagents for skin testing by Levine and Fellner, *Journal of Allergy*, 36: 342, 1965 reported tests of certain conjugates of penicillin with polylysine on human patients with a history of penicillin hypersensitivity for the purpose of studying the relative effectiveness of the various conjugates: extent of conjugation, molecular size of the conjugate, and poly-L-lysine versus poly-D-lysine of a variety of molecular sizes were equally effective in eliciting skin reactions. Moreover, the conjugates made were water insoluble and were succinylated by reaction with succinic anhydride.

Levine, *Journal of Med. Chem.* 7: 675, 1964, disclosed the preparation of penicilloyl-polylysines, by the reaction of penicillin with aqueous solutions of polylysine. The reaction products were treated with succinic anhydride (succinylated) to make them soluble and the conjugates showed optical activity. Here it was concluded that the penicilloyl groups contained in the conjugates by the reported method of preparation was entirely, or predominately, α-diastereoisomers, which contrasted to the diastereoisomeric mixtures prepared from penicillenic acids. The optical rotations of the conjugate solutions corrected for the contribution of succinylated poly-L-lysine yielded $[\alpha]_D^{25} = + 0.96°$ for $1 \times 10^{-2}$ M benzyl penicilloyl contained in a typical benzylpenicilloyl-poly-L-lysine (succinylated) conjugate. It was also reported that these particular α-diastereoisomers were at least as effective as are the diastereo-isomeric mixtures obtained from penicillenic acids.

Parker and Thiel, *J. Lab. & Clin. Med.* 62: 482, 1963, in a study comparing various penicilloyl-polylysines concluded that the benzylpenicilloyl-polylysines prepared from penicillin and penicillenic acid are generally equivalent as elicitors of cutaneous responses.

SUMMARY OF THE INVENTION

Briefly stated, the present invention is directed to a novel class of penicilloyl-polylysine conjugates, and methods for their manufacture, that are useful for eliciting cutaneous responses in persons with pencillin hypersensitivity.

There are several important desiderata to any reagent useful for detecting penicillin reactions. It is desirable, for example, to elicit a visible skin response, such as the wheal-and-erythema reaction. Furthermore, the reagent should not stimulate the formation of antibodies, otherwise the widespread use of the reagent for testing human populations would be hazardous, because the intradermal injections might create alergies of epidemic proportions. It is, therefore, an important object of the invention to develop reagents which combine effectiveness in eliciting wheal-and-erythema responses with the inability to stimulate antibody formation.

It is of considerable importance that any skin test produce a definitive and reliable reaction. While the work of previous investigators has shown promise of certain compositions for eliciting cutaneous responses, clinical testing has shown great variability in the results. See, for example, Parker et al., *J. Exp. Med.* 115: 821, 1962. In some cases, the compositions have elicited a positive reaction in patients with no sensitivity. In other cases, the compositions have not elicited any reaction, although the patient possessed a history of penicillin hypersensitivity. Further complicating the results is the fact that certain reactions are ambiguous. Reliable and definitive reactions, therefore, are yet another important object of the invention.

Many of the compositions prepared and tested heretofore have been racemic mixtures. It is one of the discoveries of the present invention that a certain group of stereo-isomers resulting from the spacial arrangement of the penicilloyl substituent in penicilloyl-polylysine conjugates possess dextro-rotary optical activity and the desired physiological properties. The other isomers may be inert, may have quite different physiological properties or side effects, or may inhibit or reduce the physiological activity of the active isomer. It is still yet another object of the invention, therefore, to provide compositions substantially free from the "inactive" isomers, or provide compositions containing only the active isomer. Accordingly, it is desirable to provide mixtures of the stereo-specific isomers, and process for their preparation.

The reagents for skin testing are ordinarily administered in buffered saline solutions. Accordingly, it is desirable that the compositions be water soluble at a pH of 7 to 8. Water solubility of penicilloyl-polylysine conjugates has been obtained heretofore by succinylation. See, for example, Levine and Fellner, supra. It is, therefore, a further object of this invention to provide compositions that are water soluble at a neutral pH without succinylation.

It is still a further object of the invention to provide a high degree of substitution of penicilloyl groups in the polylysine. In addition, it is desirable to provide penicilloyl-polylysine conjugates which are stable in solution upon standing for long periods of time.

It has now been discovered that novel mixtures of the pencilloyl-polylysine conjugates, as more particularly defined in the appended claims, are useful for eliciting cutaneous responses in persons with penicillin hypersensitivity and fulfill at least some of the objectives set forth hereinabove.

DESCRIPTION OF THE PREFERRED EMBODIMENTS

According to this invention certain mixtures of water soluble penicilloyl-polylysine conjugates having a specific optical rotation (measured as hereinafter defined) greater than + 100° have been found to be particularly satisfactory reagents in the elicitation of cutaneous responses in persons having penicillin hypersensitivity. These mixtures comprise the dextro-rotary stereoisomeric penicilloyl-polylysine conjugates represented by the following formula:

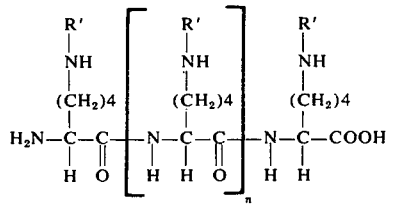

wherein $n$ is an integer greater than 10 usually from about 10 to about 100, and preferably from about 20 to about 50; and $R'$ is H or penicilloyl substituents as represented by the following formula:

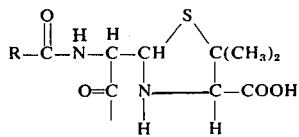

wherein R is selected from the group consisting of benzyl, allylthiomethyl, phenoxyethyl, 2,6-dimethoxyphenyl, 5-methyl-3-phenyl-4-isoxazoyl, 5-methyl-3-ortho-chlorophenyl-4-isoxazolyl, 6-(2-ethoxyl-1)-naphthyl, and alpha-aminobenzyl, and wherein at least about 40% of the $R'$ groups are the above penicilloyl substituents.

The penicilloyl-polylysine conjugates of the invention desirably have a high ratio of penicilloyl substituents to the epsilon-amino groups of the polylysine. Low amounts of penicilloyl substitution in the polylysine conjugates tends to sensitize the patient, and for this reason at least about 40%, and most desirably at least about 50%, of the epsilon-amino groups of the polylysine are conjugated with penicilloyl substituents. Water solubility of the conjugates restricts the upper limit of penicilloyl substitution. The conjugates are further characterized in that the alpha-carbonyl of penicillin is linked to the epsilon-amino group of the polylysine through an amide bond.

The penicilloyl-polylysine conjugates of the invention are mixtures of the dextro-rotary stereoisomers. Optical rotation of mixtures of the conjugates of the invention in solutions corrected for the contributions of the polylysine yields a specific rotation in excess of $[\alpha]_D^{25} > + 100°$ for $1 \times 10^{-2}$M benzylpenicilloyl-polylysine conjugate, and preferably yields a specific rotation in excess of $[\alpha]_D^{25} > + 150°$, and most desirably yields a specific rotation in excess of $[\alpha]_D^{25} > + 200°$ for the foregoing conditions.

The dextro-rotary penicilloyl-poly-L-lysine conjugates having the properties characterized above are preferred, although the invention also contemplates the dextro-rotary penicilloyl-poly-D-lysine conjugates.

Many of the penicilloyl-polysine conjugates prepared by prior investigators have been water insoluble, and water solubility has been achieved only by succinylation, e.g., Levine, supra. The particular penicilloyl-polylysine conjugates of the invention are water soluble, without succinylation, at ambient temperatures.

The present invention also relates to the discovery of processes for the manufacture of the penicilloyl-polylysine conjugates. The processes of preparation are characterized by the reaction of neutralized polylysine hydrochloride with penicillin in a non-aqueous polar solvent. Polylysine is insoluble in most non-aqueous solvents. One important feature of the invention is the disclosure of non-aqueous solvents in which both polylysine and penicillin are soluble, and in which penicillin is stable and yet reacts with polylysine.

In one preferred embodiment, the polylysine hydrochloride is dissolved in the non-aqueous polar solvent, for example, dimethyl sulfoxide, and neutralized, such as with an amino-compound, for example, a tertiary amine. The neutralized polylysine hydrochloride is then reacted with penicillin. The reaction may be carried out at ambient temperatures.

The non-aqueous solvent is one in which the penicillin is stable. Ordinarily penicillin is indefinitely stable as a salt in the solid state, but when dissolved in an aqueous neutral solution, it remains stable only for a few hours at room temperature and is irreversibly transformed into penicillenic acid and penicilloic acid. The deterioration is hastened by raising the pH and both the optical isomers are obtained. The discovery of using a non-aqueous polar solvent in which the penicillin is stable during the reaction is an important aspect of the invention. By carrying out the conjugation in a non-aqueous polar solvent, the deterioration of penicillin and formation of side products during the reaction can be practically avoided.

In addition, it has been discovered that the use of a non-aqueous polar solvent promotes a most important stereo-specific reaction in which the dextro-rotary conjugate is formed. The non-aqueous polar solvent also dissolves the polylysine hydrochloride which facilitates the reaction. Polylysine is insoluble in most non-aqueous solvents. Only a few polar solvents will dissolve it. Most organic solvents are not suitable.

Non-aqueous polar solvents suitable for use in the practice of the invention include dimethyl sulfoxide, dimethyl formamide and formamide. Special preference is given to dimethyl sulfoxide.

The polylysine hydrochloride employed in the reaction may have an average molecular weight of about 5,000, usually at least 2,000, and ordinarily in the range from about 2,000 to about 10,000. The $n$ in the formula given above is at least about 10 and between about 10 to about 100, and preferably from about 20 to about 50.

The polylysine hydrochloride is neutralized with a neutralizing agent prior to the reaction with penicillin. The neutralizing agents are compounds soluble in the non-aqueous polar solvent, which will react with and neutralize the polylysine hydrochloride, and which will not react with the penicillin. Suitable neutralizing agents include the nitrogen-bearing compounds, the most common of which are the amino compounds, preferably the tertiary amines, as for example, triethyl amine. Preferably, the polylysine hydrochloride is dissolved in the non-aqueous polar solvent and a molar excess of tertiary amine neutralizing agent over polylysine hydrochloride is added in the neutralizing step.

The polylysine hydrochloride may be either the poly-L-lysine or the poly-D-lysine hydrochloride. Special preference is given to the poly-L-lysine in order to form the preferred penicilloyl-poly-L-lysine conjugates, although for some purposes it may be desirable to use poly-D-lysine hydrochloride.

Penicillin, as the term is used herein, refers to any of the various penicillin compounds and their various salts, including benzylpenicillin, and other penicillin compounds in which the benzyl group is replaced by other substituents, such as, allylthiomethyl, phenoxyethyl, phenoxymethyl, dimethoxyphenyl, 5-methyl-3-phenyl isoxazolyl, 5-methyl-3-ortho-chlorophenyl-4-isoxazolyl, 2-ethoxy-1-naphthyl, α-aminobenzyl. Some of the penicillin compounds are more desirable than others, and special preference is given to potassium benzylpenicillin (known as potassium penicillin G).

Table I shows the chemical name and formula for some of the penicillin compounds suitable for use in the practice of this invention.

TABLE I

| "R" Group | Suitable "R" Groups for Penicillin Backbone Chemical Name |
|---|---|
| 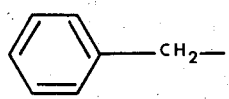 | Benzyl |
| 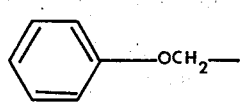 | Phenoxymethyl |
| 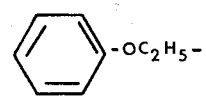 | Phenoxyethyl |
| 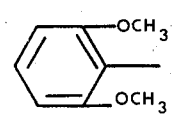 | Dimethoxyphenyl |

TABLE I-continued

| "R" Group | Suitable "R" Groups for Penicillin Backbone Chemical Name |
|---|---|
| | 5-methyl-3-phenyl-4-isoxazolyl |
| | 5-methyl-3-ortho-chlorophenyl 4-isoxazolyl |
| | 2-ethoxy-1-naphthyl |
| | Alpha-aminobenzyl |
| $CH_2=CH-CH_2-S-CH_2-$ | Allythiomethyl |

The process for preparing the conjugates of this invention can be carried out with any of the various penicillin compounds, since the ultimate usefulness of the conjugates in determining penicillin sensitivity depends on the size of the polylysine chain and the percentage conjugation or substitution, rather than on the specific penicillin used.

The reaction between the neutralized polylysine hydrochloride and penicillin may be performed at ambient temperatures and pressures, for example at temperatures broadly within the range from about 70°F to about 140°F at ambient pressures. Ordinarily 3 to 10 hours will complete the reaction, although lesser or greater times may be used as may be necessary when the temperature is varied.

During the reaction, the penicilloyl-polylysine conjugates may be formed as a soluble product in the reaction solvent. The soluble product is made insoluble by addition of acetone, and the acetone insoluble product separated from the solvent, as by centrifugation or filtration.

EXAMPLES

The compositions and process of this invention are further illustrated by the following examples.

EXAMPLE I

Poly-L-lysine hydrochloride (3.45 g.) was added to a 500 ml. flask containing 250 ml. of purified dimethyl sulfoxide. The mixture was stirred until poly-L-lysine hydrochloride completely dissolved into dimethyl sulfoxide. After the poly-L-lysine hydrochloride had dissolved, triethyl amine (66 ml.) was added to the mixture drop by drop. The mixture was stirred for additional 15 minutes to allow uniform mixing. 35 g. of potassium penicillin G was added in small portions to the reaction mixture, and the addition of penicillin was completed in one hour. The reaction mixture was stirred in an atmosphere of $N_2$ for next 8 hours, at the end of this period an additional 10 g. of potassium penicillin G was introduced into the flask and the reaction was allowed to proceed for another 12 hours. Undissolved, excess penicillin G was removed by vacuum filtration and the clear filtrate was transferred into 4 liter Erlenmeyer flask, fitted with an overhead stirrer. 2000 ml. of acetone was slowly added and the mixture was stirred under nitrogen atmosphere for 30 minutes. Penicilloyl-polylysine precipitates were colloidal in nature giving it a milky look. The precipitates were centrifugated in a refrigerated centrifuge maintained at 15°C. Precipitates were washed with 300 ml. of cold acetone and the precipitates were then dissolved in 200 ml. of deareated 0.01 M phosphate buffer, pH 7.6.

Dialysis

The penicilloyl-poly-L-lysine conjugate solution (200 ml.) was divided into four 50 ml. portions for dialysis. Each dialysis tube (union Carbide, size 20) 15 inches long was closed at one end. A 50 ml. portion of the conjugate was introduced into each tube and the other end was closed leaving enough empty space in the bag for diffusion of water. The bags were suspended on a rotating wheel that was placed over a 18 × 6 inch glass jar containing 5 l. of 0.01 M phosphate buffer, pH 7.6. An efficient dialysis was achieved by rotating the wheel at 12 rpm. Buffer was changed every 6 hours. The dialysate was analyzed at every buffer change for penicilloyl content. When penicilloyl content dropped to about $1.0\ 33\ 10^{-8}M$, dialysis was discontinued, dialysis bags were opened and the conjugate was sterilized by passing it through milipore filters. The conjugate was stored in a sterile bottle under nitrogen atmosphere at 4°C.

EXAMPLE II

Description of the Product

A preparation of penicilloyl-poly-L-lysine conjugates was made from a polylysine hydrochloride with average molecular weight between 7,000 and 10,000 in purified dimethyl sulfoxide. The penicilloyl-poly-L-lysine used for optical rotation studies and skin testing contained penicilloyl groups on 55% of the epsilon-amino residues of polylysine. This preparation is free of penamaldate residues (concentration less than 0.5%) and penicillenic groups as determined by U. V. absorption spectrum.

Analysis

Optical rotation measurements were conducted on Perkin Elmer Polarimeter model No. 141, using a one decimeter micro cell. The penicilloyl-polylysine solution was dissolved in 0.01 M phosphate buffer, pH 7.6. The optical rotation was +0.725° at a concentration of 0.004714 g per ml. The concentration of penicilloyl residues was determined by spectro-photometric titration with $HgCl_2$ at pH 8.0, using a molar extinction coefficient of 23,500. The observed rotation of the conjugate is composed of: (1) rotation of benzylpenicilloyl moiety, (2) rotation of polylysine back bone. The true rotation by benzylpenicilloyl groups may be obtained by correcting for the rotation by polylysine. This was done by: (1) hydrolyzing the benzylpenicilloylpolylysine solution (the same solution as used for optical rotation) with 6.0 N HCl and analyzing for lysine concentration by Beckman Spinco Amino acid Analyzer. (2) Determining the optical rotation of an aliquot of the same concentration of polylysine in 0.01 M phosphate buffer pH 7.6. The rotation was found to be − 0.2776. Therefore, the true rotation of benzylpenicilloyl moiety will be = 0.7250 − (−0.2776). The true optical rotation was:

$\alpha = +1.0026$ at a concentration of 0.004714 g/ml in a one decimeter tube

This specific rotation of benzylpenicilloyl moiety:

$$[\alpha]_D^{25} = \frac{\text{actual rotation}}{\text{length of the tube} \times \text{concentration in grams per ml. in decimeters}}$$
$$= \frac{1.0026}{1 \times 0.004714}$$
$$[\alpha]_D^{25} = +212.68$$

EXAMPLES 3–10

The procedures of Examples 1 and 2 are repeated except that the following penicillin compounds are used in place of benzyl penicillin (penicillin G):

| Example | Penicillin |
|---|---|
| 3 | Phenoxymethyl Penicillin |
| 4 | Phenoxyethyl Penicillin |
| 5 | Dimethoxyphenyl Penicillin |
| 6 | 5-Methyl-3-phenyl-4-isoxazolyl Penicillin |
| 7 | 5-Methyl-3-ortho-chlorophenyl-4-isoxazolyl Penicillin |
| 8 | 2-Ethoxy-1-naphthyl Penicillin |
| 9 | Alpha-aminobenzyl Penicillin |
| 10 | Allylthiomethyl Penicillin |

EXAMPLE 11

The procedures of Example 1 and 2 are repeated except that poly-D-lysine hydrochloride is employed in place of poly-L-lysine hydrochloride.

One of the uses for the conjugates of this invention is in skin testing for penicillin hypersensitivity. The conjugated compositions are prepared for skin testing by first dissolving the composition in buffered isotonic solutions, having a pH in the range from 7 to 8. For example, the conjugates prepared above may be diluted with aqueous solutions 0.15 M NaCl in 0.01 M phosphate, pH 7.6. In addition, other physiological salt solutions may be used.

Intradermal injections may be made of the foregoing solutions with a 26 guage needle, the volume injected may be generally about 0.01 to 0.03 cc. Alternatively, the conjugate may be applied by the scratch test technique. The development of a wheal at the injection site after about 20 minutes indicates a positive reaction, and penicillin hypersensitivity.

UTILITY

Penicillin hypersensitivity tests carried out with the conjugate compositions of this invention reflect the numerous advantages of penicillin hypersensitivity determinations made with such compositions. For example, Table II illustrates a comparison of the sensitivity detection effectiveness of the stereoisomeric penicilloyl-poly-L-lysine compositions of our invention with a mixture of stereoisomers. In Table II the distribution of skin reactions is shown by history of penicillin therapy and hypersensitivity. Table III, on the other hand, shows the results of a comparison of skin tests conducted with the stereoisomeric penicilloyl-poly-L-lysine compositions and penicillin-G. It is of particular interest in examining the data presented in Table II to note that the sensitivity tests performed with the stereospecific penicilloyl-poly-L-lysine compositions of the invention exhibit a vastly reduced amount of ambiguity in determining sensitivity. (See column 2, for example, showing the percentages of patients tested who had neither a positive nor negative skin test.)

pated that if such a correlation could be demonstrated, that the skin tests would be a valuable procedure in anticipating such reactions, and/or avoiding serious and possibly fatal anaphylaxis.

Twenty-six clinical investigators contributed a total of 1160 cases to the evaluation. Patients were tested according to a protocol as follows:

1. All patients being subjected to allergy investigation were to be tested for penicillin hypersensitivity. Two preparations were to be used. These are:
    1. Penicilloyl-polylysine (PPL) prepared by the procedure set forth in Example I and as identified in Example II in a concentration of $6 \times 10^{-5}$ M (Penicilloyl).

TABLE II

| PENICILLIN THERAPY & SENSITIVITY | | NEGATIVE SKIN TESTS | | NEITHER NEGATIVE NOR POSITIVE SKIN TESTS | | POSITIVE SKIN TESTS | | TOTALS | |
|---|---|---|---|---|---|---|---|---|---|
| | | No. | % | No. | % | No. | % | No. | % |
| GROUP I: Claimed prior history of non-sensitivity and previous penicillin Treatments | A. | 4223 | 91.5 | 36 | 0.7 | 358 | 7.8 | 4617 | 100 |
| | B. | 835 | 26.4 | 1430 | 45.2 | 897 | 28.4 | 3162 | 100 |
| GROUP II: Claimed prior history of sensitivity and previous penicillin treatments | A. | 143 | 77.7 | nil | nil | 41 | 22.3 | 184 | 100 |
| | B. | 37 | 19.0 | 85 | 43.6 | 73 | 37.4 | 195 | 100 |
| GROUP III: No prior history of sensitivity and no previous penicillin treatments | A. | 637 | 96.5 | 1 | 0.2 | 22 | 3.3 | 660 | 100 |
| | B. | 171 | 40.7 | 155 | 36.9 | 94 | 22.4 | 420 | 100 |
| TOTALS | A. | 5003 | 91.6 | 37 | 0.7 | 421 | 7.7 | 5461 | 100 |
| | B. | 1043 | 27.5 | 1670 | 44.0 | 1064 | 28.0 | 3797 | 100 |

A.= Patients tested with the "Monostereoisomeric" Penicilloyl Poly-L-lysine, prepared by the procedure set forth in Example I and as identified in Example II.
B.= Patients tested with a mixture of stereoisomers having negligible optical rotation.

TABLE III

| | Penicilloyl-Poly-L-lysine Positive Skin Tests | Penicillin G. Positive Skin Tests | Total Positive Skin Tests | Tested Total |
|---|---|---|---|---|
| Number of Patients | 209 | 166 | 266 | 1163 |
| % | 17.9 | 14.3 | 22.9 | |

(Chi Square: 5.876)
($P = <0.02$)

The following data illustrate the penicillin sensitivity detection effectiveness of the stereoisomeric penicilloyl-poly-L-lysine compositions of the invention by comparison with the sensitivity effectiveness of penicillin G.

Additional tests were conducted to determine whether or not there was a significant correlation between skin tests to penicillin substances, and clinical evidence of penicillin hypersensitivity. It was antici- 2. Penicillin G (Benzyl Penicillin) in a concentration of 10,000 units per cc.

For maximum safety, it was recommended that the tests first be done by the scratch technique. Intradermal tests were then to be done on those showing negative scratch tests. In cases where the penicillin sensitivity was suspected to be of a violent character, more dilute reagents were recommended at the discretion of the individual investigator.

A uniform technique was recommended for the performance of the intradermal tests. Only a minimal amount of testing reagent was to be injected so as to make a barely discernible intradermal bleb. The amount necessary for this injection is about 0.01 to 0.03 cc. It was recognized that the intrepetation of the test results is an important matter. The reactions were to be recorded in terms of (1) the time required for the appearance of a reaction, (2) the size of erythema and (3) the size of whealing. These were to be recorded as actual measurements. Some objective measurement of dermographism was also to be recorded.

It was also contemplated that all patients who were to be treated with penicillin be tested as recommended above, even though they had previously received penicillin with impunity.

A comprehensive clinical history was takan on each patient with particular regard to previous penicillin therapy, and reaction.

In order to properly analyze the data on such a large number of patients, a data processing system was utilized.

Analysis of the data indicated the following significant correlations, details of which will be presented:
1. Correlation of skin tests to Pen G and PPL with clinical history of a penicillin reaction.
2. Correlation of time of occurrence of reaction following the penicillin administration with the skin test responses.
3. Correlation of the type of hypersensitivity reaction (visceral or skin), with the skin test responses.
4. Correlation of the reaction to penicillin challenge following skin testing with skin test response and history of previous penicillin allergy.
5. Correlation of skin test responses with reason for testing, i.e. to penicillin, or to other substances.
6. Correlation of skin test results in patients having received only one dose of penicillin with patients having histories of multi-course therapy.
7. Correlation of non-therapeutic contact with penicillin with skin test response.

No significant correlation was found regarding:
1. Route of administration.
2. Family history of allergy.
3. Personal history of allergy.
4. Correlation of skin tests with occupation.

Details of these analyses are now given.

Table IV summarizes the skin test results on all patients, without regard to other specific factors. It will be noted that the overall positivity rate was higher for PPL than for Pen G (P =<.01). It will also be noted that a significant number of patients reacted only to PPL, and another group only to Pen G. Therefore, to detect the maximum number of reactors, both test reagents would be required. A technical problem was classification of the ambiguous or borderline reactors, particularly those showing only erythema. Attempts to correlate the appearance of the erythematous flare without wheal formation with a history of penicillin hypersensitivity were unsuccessful. In some instances, however, erythema without wheal did appear to be associated with hypersensitivity to the antibiotic. The time of development of erythema without wheal varied widely from a few minutes to more than 7 days which also made its importance questionable. as a diagnostic sign. For these reasons erythema alone responses were counted with the negatives. In some instances, however, data will be presented in which erythema without wheal are counted as positive responses (figures appearing in parentheses).

Table V. The results of skin tests on patients who have shown previous hypersensitivity reactions are compared with those who had no such reactions. Also included in this table are analyses of those who have received no previous penicillin and on whom no therapeutic history could be obtained.

Conclusions: Patients who have had previous penicillin reactions (Group II) show a significantly higher positivity rate for both reagents than those who have had no such reactions following therapy (P= <0.001 for both reagents). The positivity rate was significantly higher to PPL than to Pen G (P= <0.05).

TABLE IV

DISTRIBUTION OF SKIN REACTIONS TO PENICILLOYL-POLYLYSINE (PPL) AND PENICILLIN G (PG)

| PPL (+) PG (−) | | PPL (+) PG (+) | | PPL (−) PG (+) | | PPL (−) PG (−) | |
|---|---|---|---|---|---|---|---|
| No. | Percent | No. | Percent | No. | Percent | No. | Percent |
| 79 (105)* | 6.9 (9.1) | 34 (80) | 3.0 (6.9) | 38 (49) | 3.3 (4.3) | 1002 (919) | 86.9 (79.7) |

TOTALS

| PPL (+) | | PG (+) | | TOTAL (+) | | TOTAL TESTED | |
|---|---|---|---|---|---|---|---|
| No. | Percent | No. | Percent | No. | Percent | No. | Percent |
| 113 (185) | 9.8 (16.1) | 72 (129) | 6.2 (11.2) | 151 (234) | 13.1 (20.3) | 1153 | 100 |

*Skin reactions recorded as "erythema only" were classified as ambiguous. Figures in parentheses show distributed of skin reactions when ambiguous responses were counted as positive skin reactions.

TABLE V

DISTRIBUTION OF SKIN REACTIONS TO PENICILLOYL-POLYLYSINE (PPL) AND PENICILLIN-G (PG) BY HISTORY

| | Skin Test (+) | | | | Skin Test (−) | | | |
|---|---|---|---|---|---|---|---|---|
| | PPL | | PG | | PPL | | PG | |
| BY HISTORY: | No. | Percent | No. | Percent | No. | Percent | No. | Percent |
| Group I (675 Patients) (Penicillin Rx no hypersensitivity) | 36 (78) | 5.3 (11.6) | 24 (56) | 3.6 (8.3) | 639 (597) | 94.7 (88.4) | 651 (619) | 96.4 (91.7) |

TABLE V-continued

DISTRIBUTION OF SKIN REACTIONS TO PENICILLOYL-POLYLYSINE (PPL)
AND PENICILLIN-G (PG) BY HISTORY

| BY HISTORY: | Skin Test (+) PPL No. | Skin Test (+) PPL Percent | Skin Test (+) PG No. | Skin Test (+) PG Percent | Skin Test (−) PPL No. | Skin Test (−) PPL Percent | Skin Test (−) PG No. | Skin Test (−) PG Percent |
|---|---|---|---|---|---|---|---|---|
| Group II (352 patients) Penicillin Rx & hypersensitive) | 73 (97) | 20.7 (27.6) | 47 (65) | 13.4 (18.5) | 279 (255) | 79.3 (72.4) | 305 (287) | 86.6 (81.5) |
| Group III (70 patients) (No Penicillin Rx in Past) | 1 (6) | 1.4 (8.6) | — (5) | — (7.1) | 69 (64) | 98.6 (91.4) | 70 (65) | 100.0 (92.9) |
| Group IV (56 patients) (No Data) | 3 (4) | 5.4 (7.1) | 1 (3) | 1.8 (5.3) | 53 (52) | 94.6 (92.9) | 55 (53) | 98.2 (94.6) |
| TOTALS: (1153 patients) | 113 (185) | 9.8 (16.0) | 72 (129) | 6.3 (11.2) | 1040 (968) | 90.2 (84.0) | 1081 (1024) | 93.8 (88.8) |

Skin reactions recorded as "erythema only" were classified as ambiguous. Figures in parentheses show distribution of skin reactions when ambiguous responses were counted as positive skin reactions.

TABLE VI

DISTRIBUTION OF SKIN RESPONSES BY HISTORY OF TIME OF REACTION
AFTER ADMINISTRATION OF THERAPEUTIC PENICILLIN

| Time of Penicillin Reaction Post Therapy | SKIN RESPONSES PPL (+) PG (−) No. | PPL (+) PG (−) Percent | PL (+) PG (+) No. | PL (+) PG (+) Percent | PPL (−) PG (+) No. | PPL (−) PG (+) Percent | PPL (−) PG (−) No. | PPL (−) PG (−) Percent |
|---|---|---|---|---|---|---|---|---|
| Within 30 Minutes (56 patients) | 14 (16)* | 25.0 (28.6) | 12 (15) | 21.4 (26.8) | 5 (5) | 8.9 (8.9) | 25 (20) | 44.6 (35.7) |
| Between 30 minutes and 24 hours (87 patients) | 9 (10) | 10.4 (11.5) | 12 (14) | 13.8 (16.1) | 5 (7) | 5.7 (8.0) | 61 (56) | 70.0 (64.4) |
| More than 24 hours (144 patients) | 16 (22) | 11.1 (15.3) | 8 (11) | 5.6 (7.6) | 9 (11) | 6.2 (7.6) | 111 (100) | 77.1 (69.4) |

*Skin reactions recorded as "erythema only" were classified as ambiguous. Figures in parentheses show distribution of skin reactions when ambiguous responses were counted as positive skin reactions.

Very significant is the correlation of positive skin tests to the time of reaction following penicillin administration. Table VI shows the distribution of skin test responses by history of time of reaction after the administration of therapeutic penicillin. These data indicate the highest incidence of skin reactivity in patients with histories of immediate reactions (within 30 minutes) to penicillin as compared with patients developing reactions after 24 hours. In the immediate reacting group, 26/56 (46%) exhibited positive skin tests to PPL, while 17/56 (30.4%) were positive to Pen G. A total of 31/56 (55.5%) were positive to one or the other, or both reagents. Of the delayed (after 24 hours) group, 24/144 (16.7%) were positive to PPL, while 17/144 (11.8%) were positive to Pen G. A total of 33/144 (22.9%) were positive to one or both reagents in this group. This difference in the fast and slow reacting group is significant (P=<0.001). These data also suggest a greater reliability of the skin testing procedure in patients with history of reaction to penicillin within 30 minutes as opposed to patients whose reaction to penicillin occurred after 24 hours. The percentage of positivity for the group who had fast reactions was over twice that of the group who developed delayed reactions (55.4% vs. 22.9%). No ready explanation of why certain patients in both groups failed to develop positive responses to either of the reagents is apparent.

Table VII shows the distribution of positive tests in skin reactive, penicillin hypersensitive patients. Note in the group of patients with history of reaction to penicillin within 30 minutes, that up to 83.9% responded to PPL, while 54.8% responded to Penicillin G skin tests. This difference is significant, (P=<0.02). In like manner, patients who developed reactions to penicillin after 24 hours, responded up to 72.7% with PPL and to 51.5% with Penicillin G. This difference, however, is not significant (P=<0.10). If, however, ambiguous responses are counted with positive tests, the difference between the reagents becomes significant, (P=<0.02).

Since fast reactions (immediate and up to 30 minutes) almost invariably represent anaphylaxis, the correlation with positive skin tests in this group is of great significance. Although the number of positive reactions to PPL is significantly higher than to Penicillin G, the maximum number of reactors will be picked up only when both reagents are used.

The reaction to challenge is indicated in Table VII. It will be noted that of 5 patients positive to PPL, one reacted on challenge. Of four positive to penicillin G, one reacted to challenge. Of 92 patients negative to both reagents, one reacted to challenge.

No conclusions are drawn from these data because of the minimal number of positive skin reactors challenged. This series would be expected to be small because of the potential hazards of giving penicillin to patients having known positive skin tests. The occurrence of reactions in two of the test positive patients is suggestive of the danger of administering penicillin to such patients.

Table IX shows the analysis of the skin test responses by history of the type of hypersensitivity reaction experienced, i.e. visceral or skin. It will be noted that the positivity rate is significantly higher in both categories than in patients who had tolerated penicillin therapy without any reaction. PPL appeared to give significantly higher positivity rate than Pen G with regard to skin reactions (P= <0.002). The positivity rate for Pen G was higher for visceral than for skin reactions (P=

<0.001). The difference, however, in skin reactivity between PPL and Pen G in patients who had experienced visceral reactions is not significant.

Patients were analyzed (Table X) with regard to the reason for testing. One group was stated to be specifically tested because of suspected allergy to penicillin and this was compared with the group that was tested for suspected allergy to other substances. The group being specifically tested for penicillin hypersensitivity showed a highly significantly increased incidence of positive skin tests than the patients tested for hypersensitivity to other substances (P= <0.001). The difference in skin responses to PPL and Pen G in the "Penicillin" group is not significant but difference in response to the two reagents in the "other substances" group is significant (P= <0.05).

The analysis of data on penicillin handlers indicates a correlation with positive skin responses to both reagents, (P= 0.02). This likewise might be anticipated.

Of possible importance is the high incidence of positive skin reactions in those patients having had only one dose of penicillin (Table XI). The differences in skin reactivity to both reagents in patients receiving one dose as compared with one course or multicourses of penicillin is significant (P= <0.001 and <0.002, respectively). Although these data suggest that one dose is more likely to sensitize than a course of penicillin, it may also indicate that penicillin was discontinued because of suspected sensitivity after one dose.

Discussion and Conclusions

There are certain inherent problems in tests of this sort due to (1) the number of investigators, (2) deviation from adherence to the protocol, (3) large dependence on the accuracy of previous medical records, and (4) histories as given by the patient. The most serious source of error is the history of previous penicillin reaction as stated by the the patient. Direct examination of the patient records revealed instances where the history was inadequate or difficult to interpret and suggests that there may be an even better correlation between history of hypersensitivity and skin tests response than is revealed by the figures. The patient is given penicillin because of an illness. Any untoward reaction that occurs after penicillin administration is likely to be attributed to the penicillin, whereas it is quite probable that many of these untoward reactions are, in fact, a symptom or complication of the illness. This is particularly true of rashes of various sorts. Urticarial rashes, erythema multiform, and other toxic rashes commonly occur in the course of various viral or streptococal infections, which would be difficult to differentiate from true penicillin reactions. Similar problems may occur in the differentation of gastrointestinal and pulmonary complaints. Well defined anaphylactic reactions are not likely to be misdiagnosed.

Another problem is the interpretation of skin tests. The significance of minimal reactions, particularly erythema without edema has not been established. Generally, significant positive skin tests are well defined, and show a large central wheal. The equivocal test, as unexemplified by erythema alone, develops so erratically that its significance is not clear.

Even allowing for the problems and inherent inaccuracy of the tests, the results permit the following conclusions: (1) Skin Testing to Pen G and to PPL is safe and of value. (2) Results of skin tests show a significant correlation to history of clinical penicillin hypersensitivity. (3) The skin test reaction rate is particularly high in patients who experienced penicillin reactions of the immediate type within 30 minutes (Table VI). In these patients, 26/56 (46.5%) exhibited positive skin tests to PPL, while 17/56 (30.4%) were positive to Penicillin G. A total of 31/56 (55.5%) were positive to one or the other, or both reagents. (4) In the immediate reactor group, analysis of those patients having positive skin tests (Table VII) indicates that 84% were positive to PPL, while 55% were positive to Pen G. This would indicate that in this group 16% would be missed if only PPL were used as a skin test antigen, while 45% would be missed if only Pen G were used. The necessity of using both reagents for testing, therefore, seems obvious and suggests a high degree of accuracy with regard to correlation of skin tests in immediate hypersensitivity reactions. Since these are the most dangerous type of penicillin reactions, often including anaphylaxis, it would be anticipated that such skin testing procedures performed before the administration of therapeutic penicillin would be valuable in preventing and avoiding such reactions. (5) Lack of a 100% correlation of skin tests with clinical history points up the importance of authenticating clinical history of penicillin reactions. The number of patients challenged was insufficient to draw any conclusions as to which is the more predictive, clinical history or skin testing. (6) Patients who have had authenticated penicillin reactions are known to be likely candidates for subsequent reactions, and such patients are not likely to receive more penicillin except under carefully controlled conditions. The real problem is the patient who has not had such a history, and who may be penicillin sensitive. Such a patient may experience a dangerous penicillin reaction, possibly fatal anaphylaxis following administration of penicillin. The data from this study suggest that such dangerous reactors can be identified by skin tests. It is impossible to state what percent, if not all, reactors will be identified. However, there appears no doubt that a significant number can be identified, and that needless reactions and deaths can be avoided.

TABLE VII

DISTRIBUTION OF POSITIVE SKIN TESTS IN PENICILLIN ALLERGY PATIENTS HAVING SKIN REACTIVE ANTIBODIES

| Time of Penicillin Reaction Post Therapy | TOTAL PPL (+) No. | Percent | TOTAL PG (+) No. | Percent | TOTAL POSITIVE No. |
|---|---|---|---|---|---|
| Within 30 minutes | 26 (31)* | 83.9 (86.1) | 17 (17) | 54.8 (47.2) | 31 (36) |
| Between 30 minutes and 24 hours | 21 (24) | 80.8 (77.4) | 17 (21) | 65.4 (67.7) | 26 (31) |
| More than 24 hours | 24 (33) | 72.7 (75.0) | 17 (22) | 51.5 (50.0) | 33 (44) |

*Skin reactions recorded as "erythema only" were classified as ambiguous. Figures in parentheses show distributions of skin reactions when ambiguous responses were counted as positive skin reactions.

TABLE VIII

PATIENTS CHALLENGED WITH PENICILLIN SUBSEQUENT TO SKIN TESTING WITH PENICILLOYL-POLYLYSINE (PPL) AND PENICILLIN (PG)

| | PPL+ PG+ | PPL+ PG− | PPL− PG+ | PP− PG− | TOTAL CHALLENGED |
|---|---|---|---|---|---|
| Number Challenged Number | 1 | 4 | 3 | 92 | 100 |

TABLE VIII-continued

PATIENTS CHALLENGED WITH PENICILLIN SUBSEQUENT TO SKIN TESTING WITH PENICILLOYL-POLYLYSINE (PPL) AND PENICILLIN (PG)

| | PPL+ PG+ | PPL+ PG− | PPL− PG+ | PP− PG− | TOTAL CHALLENGED |
|---|---|---|---|---|---|
| reacting to challenge | — | 1 | 1 | 1 | 3 |
| Observed by competent witness | — | 1 | 1 | 1 | 3 |

TABLE IX

DISTRIBUTION OF SKIN TEST RESPONSES BY TYPE OF HYPERSENSITIVE REACTION (i.e. SKIN vs. VISCERAL)

| | SKIN TEST RESPONSE | | | | |
|---|---|---|---|---|---|
| Type of Hypersensitivity Reaction: | PPL No. | Percent | PG No. | Percent | TOTAL TESTED Number |
| Skin | 66 | 21.4 | 39 | 12.6 | 309 |
| Visceral | 10 | 23.3 | 14 | 32.6 | 43 |
| No reactions | 36 | 5.3 | 24 | 3.6 | 675 |

TABLE X

DISTRIBUTION OF SKIN TESTS BY REASON FOR TESTING

| Reason for Testing | PPL + No. | Percent | PG + No. | Percent | TOTAL + No. | Percent | TOTAL TESTED |
|---|---|---|---|---|---|---|---|
| "Penicillin" | 31 | 12.9 | 24 | 10.0 | 34 | 18.8 | 240 |
| Other Substances | 21 | 4.5 | 9 | 1.9 | 27 | 5.8 | 463 |

TABLE XI

DISTRIBUTION OF SKIN RESPONSES IN PATIENTS BY HISTORY OF PENICILLIN THERAPY

| | Skin Reactions | | | | | | |
|---|---|---|---|---|---|---|---|
| History of Therapy | PPL− No. | Percent | PEN G− No. | Percent | TOTAL − No. | Percent | TOTAL TESTED Number |
| One Dose | 24 | 15.8 | 17 | 11.2 | 34 | 22.4 | 152 |
| One Course | 14 | 5.6 | 8 | 3.2 | 19 | 7.6 | 249 |
| Multi Courses | 14 | 7.9 | 10 | 5.6 | 22 | 12.4 | 177 |
| TOTALS | 52 | 9.0 | 35 | 6.1 | 75 | 13.0 | 578 |

Other modes of applying the principles of the invention may be employed, change being made as regards the details described, provided the features stated in any of the following claims, or the equivalent of such, be employed.

We, therefore, particularly point out and distinctly claim as our invention:

1. A composition useful for eliciting cutaneous responses in persons with penicillin hypersensitivity, comprising at least one water soluble penicilloyl-polylysine conjugate represented by the formula:

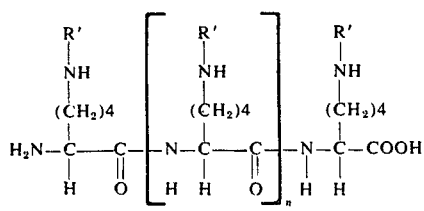

wherein: $n$ is an integer from about 10 to about 100; and

R' is selected from the class consisting of H and the penicilloyl substituents represented by the formula:

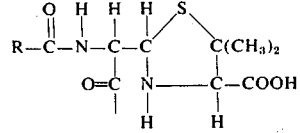

wherein R is selected from the group consisting of benzyl, allylthiomethyl, phenoxyethyl, phenoxymethyl, 2,6-dimethoxyphenyl, 5-methyl-3-phenyl-4-isoxazolyl, 2-ethoxy-1-naphtyhyl, and alpha-aminobenzyl, and in which at least 40% of said R' groups are the penicilloyl substituents;

wherein said conjugate has an optical rotation corrected for the contributions of said polylysine in said conjugate yielding a specific rotation in excess of $[\alpha]_D^{25} + 100°$ for $1 \times 10^{-2}$ M penicilloyl groups contained in the conjugate;

said conjugate is free from penamaldate and penicillenate groups;

said conjugate is soluble in water without succinylation;

said conjugate, in an effective amount, contained in a suitable pharmaceutical carrier for intra-cutaneous testing.

2. The composition of claim 1 in which the polylysine portion of said conjugate has a molecular weight of at least about 2,000.

3. The composition of claim 1 wherein the $n$ in said formula is an integer from 20 to 50.

4. The composition of claim 1 wherein R is benzyl in said the conjugate.

5. The composition of claim 1 in which the polylysine portion of said conjugate is poly-L-lysine.

6. A composition suitable for eliciting cutaneous responses in persons with penicillin hypersensitivity; comprising a mixture of
- optically active, dextro-rotary water soluble penicilloylpolylysine conjugates useful for elicitation of cutaneous responses in persons having penicillin hypersensitivity, said conjugates having optical rotation corrected for the contributions of said polylysine in said conjugates yielding a specific rotation in excess of $[\alpha]_D^{25} + 100°$ for $1 \times 10^{-2}$ M penicilloyl groups contained in the conjugate wherein;
- said conjugates are free from penamaldate and penicillenate groups;
- said conjugates are soluble in water without succinylation; and
- said conjugates, in an effective amount, contained in a suitable pharmaceutical carrier for intra cutaneous testing.

7. The composition of claim 6 in which the polylysine portion of said conjugates has a molecular weight of at least about 5000.

8. The composition of claim 6 in which at least about 40% of the epsilon-amino groups of the polylysine portion of said conjugates are linked to the alpha-carbonyl group of the penicillin through an amide bond.

9. The composition of claim 6 in which said polylysine portion comprises poly-L-lysine.

10. The composition of claim 6 wherein said penicilloyl-polylysine conjugates of said mixture comprise the benzylpenicilloyl-poly-L-lysine conjugates.

11. The composition of claim 6 in which said pharmaceutical carrier is an aqueous buffered saline solution.

12. The method of detecting penicillin hypersensitivity which comprises applying to a patient the composition of claim 1 by a scratch test technique or intracutaneous injection.

13. The method of detecting penicillin hypersensitivity which comprises applying to a patient the composition of claim 2 by a scratch test technique or intracutaneous injection.

14. The method of detecting penicillin hypersensitivity which comprises applying to a patient the composition of claim 3 by a scratch test technique or intracutaneous injection.

15. The method of detecting penicillin hypersensitivity which comprises applying to a patient the composition of claim 4 by a scratch test technique or intracutaneous injection.

16. The method of detecting penicillin hypersensitivity which comprises applying to a patient the composition of claim 5 by a scratch test technique or intracutaneous injection.

17. The method of detecting penicillin hypersensitivity which comprises applying to a patient the composition of claim 6 by a scratch test technique or intracutaneous injection.

18. The method of detecting penicillin hypersensitivity which comprises applying to a patient the composition of claim 7 by a scratch test technique or intracutaneous injection.

19. The method of detecting penicillin hypersensitivity which comprises applying to a patient the composition of claim 8 by a scratch test technique or intracutaneous injection.

20. The method of detecting penicillin hypersensitivity which comprises applying to a patient the composition of claim 9 by a scratch test technique or intracutaneous injection.

21. The method of detecting penicillin hypersensitivity which comprises applying to a patient the composition of claim 10 by a scratch test technique or intracutaneous injection.

22. The method of detecting penicillin hypersensitivity which comprises applying to a patient the composition of claim 11 by a scratch test technique or intracutaneous injection.

* * * * *